United States Patent

Wilk

Patent Number: 6,146,327
Date of Patent: Nov. 14, 2000

[54] METHOD FOR IN VIVO MEASUREMENT OF COAGULATION RATE

[76] Inventor: Peter J. Wilk, 185 W. End Ave., New York, N.Y. 10023

[21] Appl. No.: 09/129,007

[22] Filed: Aug. 4, 1998

[51] Int. Cl.[7] ................................................ A61B 5/05
[52] U.S. Cl. ......................... 600/369; 600/369; 600/370; 422/73; 128/898
[58] Field of Search ............................. 600/322, 369, 600/370, 371, 225, 425, 414, 404; 601/2; 422/73; 128/898

[56] References Cited

U.S. PATENT DOCUMENTS

| | | |
|---|---|---|
| 4,685,464 | 8/1987 | Goldberger et al. ............... 128/633 |
| 5,666,952 | 9/1997 | Fuse et al. .......................... 128/663 |
| 5,710,622 | 1/1998 | Neel et al. .......................... 356/39 |
| 5,800,781 | 9/1998 | Gavin et al. ........................ 422/73 |

*Primary Examiner*—Marvin M. Lateef
*Assistant Examiner*—Jeoyuh Lin
*Attorney, Agent, or Firm*—R. Neil Sudol; Henry D. Coleman

[57] ABSTRACT

In a method for measuring in vivo coagulation rate, a fold of organic tissues is clamped so that a target blood vessel contained in the organic tissues is closed at a downstream point and an upstream point spaced from one another. Waveform energy is then directed through the clamped organic tissues. Waveform energy transmitted at least partially through the organic tissues is analyzed to determine a state of coagulation of blood trapped in the blood vessel between the downstream point and upstream point.

17 Claims, 2 Drawing Sheets

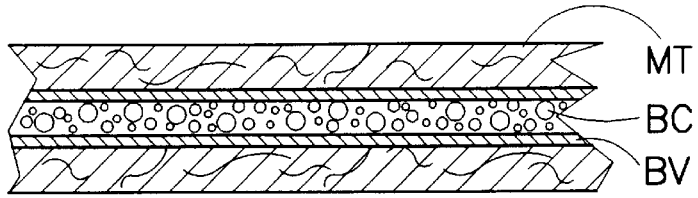
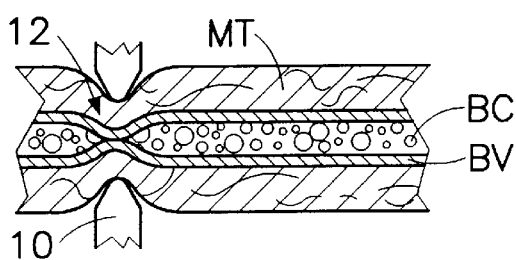
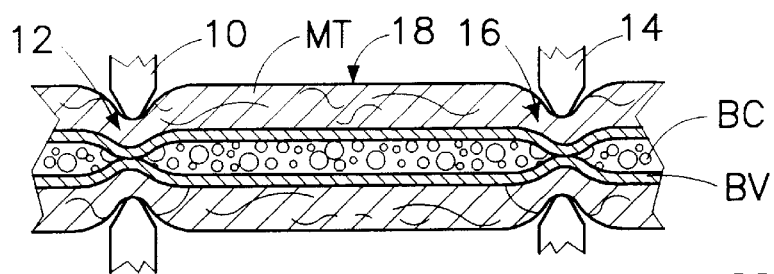
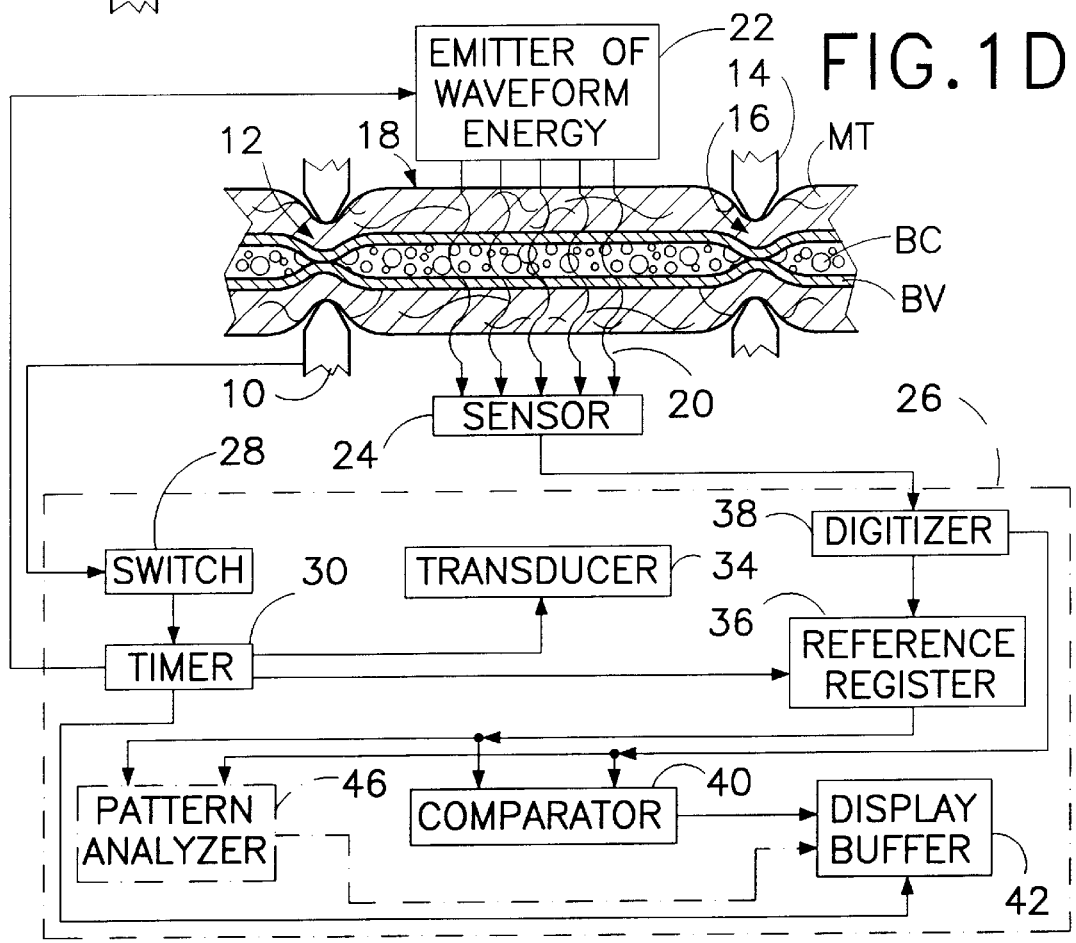
FIG. 1A
FIG. 1B
FIG. 1C
FIG. 1D

METHOD FOR IN VIVO MEASUREMENT OF COAGULATION RATE

BACKGROUND OF THE INVENTION

This invention relates to a method for measuring coagulation rate or clotting ability of a person's blood. This invention also relates to an associated device for performing an in vivo measurement of coagulation rate.

Some people's blood is prone to clotting. For example, clots may form in the vessels of the legs. This condition is known as phlebitis of the legs. Clot particles occasionally break off and flow along the venous system to the heart and from there to the lungs. In the lungs the clot may form a pulmonary embolus. If the embolus is large enough, death is the result. Less drastic effects are the collapse of a lung or a lung infection.

In other cases, patients are afflicted with an atrial fibrillation. The atria do not contract properly and some blood is not ejected but rather circulates in eddy currents in the atria and forms clots. These clots eventually pass out of the hear and may end up in the brain, resulting in a stoke. The third leading cause of death in the United States is stroke. Even if a victim does not die from a stoke, his or her brain function may become severely impaired by the death of large numbers of brain cells.

One method of treating people who are known to be afflicted with a tendency towards intravascular clot formation is to thin the blood with an anticoagulant composition such as coumadin. This composition this the blood and has no complications, when used at proper concentrations. The problem is that coumadin has a narrow range of effective concentrations. If the concentration is too low, the composition does not effectively thin the blood. If the concentration is too high, excessive bleeding results. This can be dangerous where there is even a small head trauma. The excessive bleeding produces a stroke and can result in death.

OBJECTS OF THE INVENTION

An object of the present invention is to provide a non-invasive method for measuring the coagulation rate of a person's blood. The measurement results can be used to determine the advisability of injecting a blood thinner composition.

Another object of the present invention is to provide such a method which is easy to use.

A related object of the present invention is to provide a device for the non-invasive measurement of the coagulation rate of a person's blood.

These and other objects of the present invention will be apparent from the drawings and descriptions herein.

SUMMARY OF THE INVENTION

A method for measuring in vivo coagulation rate comprises, in accordance with the present invention, clamping a fold of organic tissues so that a target blood vessel contained in the organic tissues is closed at a downstream point and an upstream point spaced from one another. Waveform energy is then directed through the clamped organic tissues. Waveform energy transmitted at least partially through the organic tissues is analyzed to determine a state of coagulation of blood trapped in the blood vessel between the downstream point and the upstream point.

The waveform energy is absorbed, reflected or refracted to different degrees depending on whether the blood trapped in the blood vessel has begun to coagulate. The onset of coagulation is detected and the time interval required for the blood to coagulate is measured.

It is contemplated that the clamping of the organic tissues is effectuated by using two clamping elements. The clamping elements are disposed on opposite sides of the fold of organic tissues and pressed towards one another to compress the tissues. The clamping elements may be connected to one another by a levered linkage for pressing the clamping elements together.

Preferably, the waveform energy is emitted from one of the clamping elements and is received by a sensor in the other clamping element after being transmitted through the fold of organic tissues.

The waveform energy is taken from the group consisting of electromagnetic radiation and mechanical vibrational energy. A source is operated in the one clamping element to generate the waveform energy.

The analyzing of the waveform energy may include the step of periodically comparing a real-time pattern of energy transmission with a reference pattern of energy transmission, thereby determining when blood trapped in the blood vessel between the downstream point and the upstream point begins to coagulate.

In accordance with another feature of the present invention, the analyzing of the waveform energy further includes the step of measuring a time interval terminating with a detection of blood coagulation in the blood vessel between the downstream point and the upstream point.

In accordance with a further feature of the present invention, the clamping of the fold of organic tissues includes the step of closing the blood vessel first at the downstream point and subsequently at the upstream point, thereby enabling a collection of an increased amount of blood in the blood vessel between the downstream point and the upstream point.

A device for measuring in vivo coagulation rate generally comprises a source of waveform energy, a sensor of the waveform energy, and an analyzer of the waveform energy is operatively connected to the source and the sensor for determining a time of onset of blood coagulation in a clamped portion of blood vessel disposed between the source and the sensor.

More specifically, a device for measuring in vivo coagulation rate comprises a first clamping element and a second clamping element, an actuator mechanism operatively connected to the first clamping element and the second clamping element for shifting the first clamping element and the second clamping element towards one another. A source of waveform energy is mounted to one of the clamping elements, while a sensor of the waveform energy is mounted to the other clamping element. An analyzer of the waveform energy operatively connected to the sensor for determining a time of onset of blood coagulation in a blood vessel clamped between a downstream point and an upstream point by the first clamping element and the second clamping element.

In accordance with another feature of the present invention, the analyzer includes a pattern comparator. The pattern comparator performs the operation, discussed above, of periodically comparing a current pattern of energy transmission with a reference pattern of energy transmission, thereby determining when blood trapped in the blood vessel between the downstream point and the upstream point begins to coagulate. The analyzer may additionally include a timer which measures the time interval terminating with a detection of blood coagulation in the blood vessel between the downstream point and the upstream point.

In accordance with an additional feature of the present invention, the clamping elements and the actuator mechanism are configured to clamp the blood vessel first at the downstream point and subsequently at the upstream point.

The clamping elements are preferably parts of a single device. Thus, the clamping of the organic tissues includes the step of actuating the device to move the first clamping element and the second clamping element towards one another differentially at the downstream point and the upstream point.

The present invention provides a method and an associated device for non-invasively measuring in vivo blood coagulation rate.

BRIEF DESCRIPTION OF THE DRAWINGS

FIGS. 1A through 1C are schematic cross-sectional views of organic tissues of an individual, showing successive steps in a method in accordance with the present invention for measuring an in vivo coagulation rate noninvasively.

FIG. 1D is partially a schematic cross-sectional view of the organic tissues of FIGS. 1A through 1C, showing another step in the method of the invention, and partially a block diagram depicting parts of a device for carrying out the method.

DESCRIPTION OF THE PREFERRED EMBODIMENTS

Figure 3:
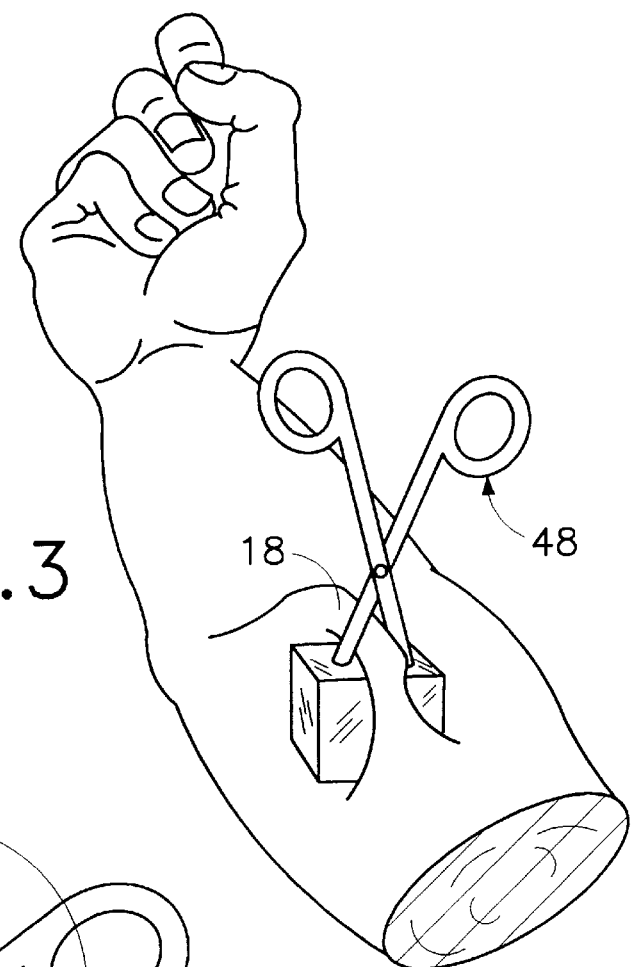
FIG. 3 is a schematic perspective view showing use of the device of FIG. 2.

FIG. 1A depicts a blood vessel BV such as a vein disposed in surrounding connective and muscle tissues MT. Corpuscles or blood cells BC are traveling with the blood flow from right to left.

In a first step of the method, illustrated in FIG. 1B, a clamp 10 is placed around tissues MT and actuated so as gently compress the tissues and occlude blood vessel BV at a downstream point 12. Blood cells BC start to accumulate just upstream of the occlusion point 12.

After a predetermined, short time period, a second clamp 14 shown in FIG. 1C is placed around tissues MT and closed to occlude blood vessel at an upstream point 16 spaced a predetermined distance from downstream point 12. The two clamps 10 and 14 trap a fold 18 of tissues MT as well as a portion of blood vessel BV.

About the time of closure of upstream clamp 16, waveform energy 20 is transmitted from an emitter or source 22 through tissue fold 18 to a sensor 24, as shown in FIG. 1D. Source 22 and sensor 24 are placed on opposite sides of fold 18, preferably in close proximity or contact therewith.

Waveform energy 20 may be electromagnetic radiation such as visible light energy or mechanical vibrational energy such as ultrasonic pressure waves. In any event, the degree of transmission of waveform energy 20 varies depending on the degree of coagulation of the blood trapped in vessel BV between downstream point 12 and upstream point 16.

A control unit 26 is operatively connected to sensor 24 for determining a point in time that coagulation effectively begins in the trapped blood. This time is a real-time measurement of the coagulation rate of the user's or patient's blood. The measured time, or a mathematical quantity related thereto, is communicated to the user/patient or medical personnel for purposes of updating a dosage of blood thinning agent to be administered.

As illustrated in FIG. 1D, control unit 26 includes a switch 28 operatively connected to clamp 10 for initiating counting operations by a timer 30 upon a closure of clamp 10 about tissues MT to effectively occlude blood vessel BV at downstream occlusion point 12. Timer 30 counts out a pre-established time interval and, at the end of the interval, transmits a signal to a transducer 34 for inducing the transducer to generate a signal cognizable by a human user. Transducer may be electroacoustic, in which case an audible signal is emitted. Alternatively or additionally, transducer 34 may be an electro-optical element, in which case a visually detectable indication is produced. The signal produced by transducer 34 alerts a user to apply clamp 14 to tissues MT to occlude blood vessel BV at upstream occlusion point 16. Alternatively, the closure of clamp 14 may be effectuated automatically in response to an actuation signal from timer 30.

Source or emitter 22 and sensor 24 are placed next to tissues MT on opposite sides of fold 18. This placement may be effectuated prior to the closure of clamp 14 or shortly thereafter. Timer 30 enables source 22 to emit waveform energy into tissues MT of fold 18 about the time that clamp 14 is closed. Substantially simultaneously with the activation of source 22, timer 30 enables a reference register 36 to store a magnitude of energy transmitted from source 22 through tissue fold 18 to sensor 24. This magnitude is encoded by a digitizer 38 connected between sensor 24 and register 36.

Figure 2:
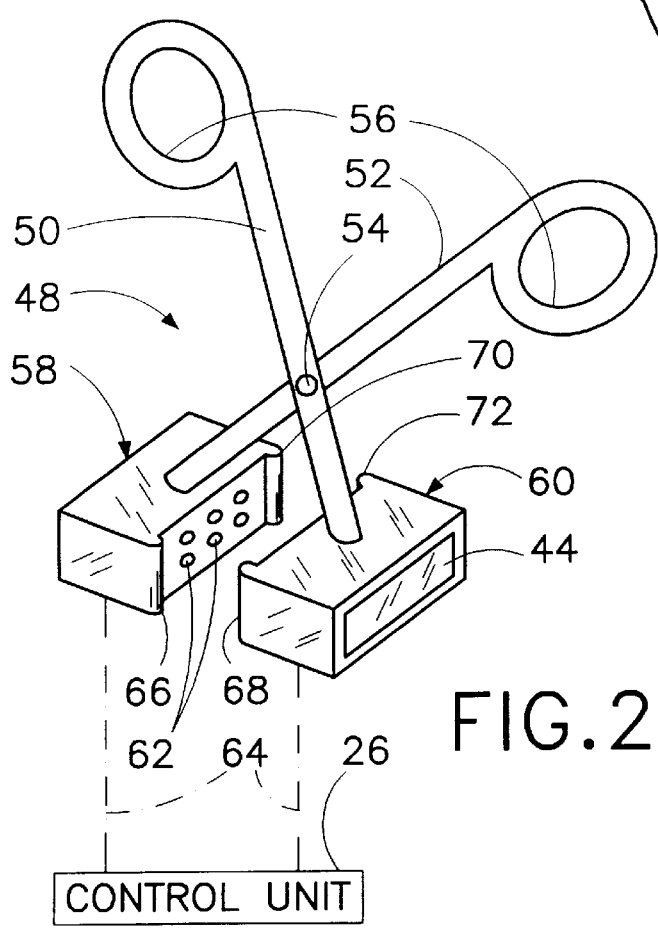
FIG. 2 is partially a schematic perspective view and partially a block diagram of the device of FIG. 1D.

An output of register 36 is connected to a comparator 40 which also receives input from sensor 24 via digitizer 38. During a measurement operation, comparator 40 continuously compares a real-time energy magnitude from sensor 24 via digitizer 38 with an initial or reference energy magnitude from register 36. These energy magnitudes are total or average energy levels detected by sensor 24. Generally, upon a commencement of coagulation in blood vessel BV between downstream point 12 and upstream point 16, the level of energy transmitted through tissue fold 18 changes detectably. Comparator 40 detects the change in transmitted energy level and activates a display buffer 42 to load a times at an output of timer 30. This time may be communicated to a user via da display 44 (FIG. 2). Alternatively or additionally, the measured time may be communicated to the user via an electroacoustic transducer or speaker (not shown). In that case, it is possible to use a speech synthesis element (not shown) to generate an audible message communicating the measured time interval to coagulation.

Control unit 26 may be provided with optional circuitry for processing the measured time interval, for example, into a recommendation for a dosage of a blood thinning agent. This recommendation or other processing result may be communicated to the user via a display or a speaker.

As further illustrated in FIG. 1D, a pattern analyzer 46 may be connected register 36 and digitizer 38 for performing a more complex operation on energy information detected by sensor 24. In that case, sensor 24 must be an array of sensing elements for generating a two-dimensional function or "picture" of energy transmission. Reference register 36 stores a multiplicity of energy level information bits together identifying an initial pattern of energy transmission through tissue fold 18. Pattern analyzer 46 processes a series of picture frames to detect a change in the pattern of energy transmission levels indicating that coagulation in blood vessel has commenced.

As illustrated in FIG. 2, the operational components of FIG. 1D may be incorporated into or coupled to an instrument 48 comprising a pair of lever arms 50 and 52 pivotably connected to one another at a pivot pin 54. At one end, each lever arm 50 and 52 is provided with a respective finger-receiving opening 56. At an opposite end, lever arms 50 and 52 carry respective clamping members or elements 58 and 60. One clamping member 58 houses waveform source 22 and is formed with emission openings or lenses 62. The other clamping member 52 holds sensor 24 and display 44. Control unit 26 may be a separate unit connected to clamping members 58 and 60 via wires 64. Alternatively, it is possible for the operating components of control unit 26 to be incorporated into clamping members 58 and 60.

Clamp 10 (FIGS. 1B–1D) is realized in the embodiment of FIG. 2 as a pair of projections or ribs 66 and 68 rigidly configured on clamping members 58 and 60. Clamp 14 takes the form of a pair of additional projections 70 and 72 at least one of which is movably mounted to its respective clamping member 58 or 60. A shifting knob (not shown) on the respective clamping member 58 or 60 is connected to the movable projection for purposes of enabling a user to actuate clamp 14 after the closure of clamp 10 as discussed above. In addition, a releasable lock may be operatively connected to the movable projection for retaining that projection in a clamping position during a coagulation measurement operation.

FIG. 3 shows the use of instrument 48 on tissue fold 18.

It is to be noted that the user should remove clamps 10 and 14 from tissue fold 18 as soon as possible after the coagulation rate measurement has been completer. To that end, control unit 26 may be connected to an electroacoustic transducer (speaker) or a light source for generating an alert or alarm signal to induce the user to remove clamps 10 and 12 from the skin. Alternatively, control unit 26 may be operatively connected to clamps 10 and 12 to automatically disengage or unlock those elements upon the completion of a coagulation rate measurement. In this way, the coagulation in blood vessel BV between downstream poitn 12 and upstream point 16 cannot advance sufficiently to form a permanent, undissolvable clot.

Although the invention has been described in terms of particular embodiments and applications, one of ordinary skill in the art, in light of this teaching, can generate additional embodiments and modifications without departing from the spirit of or exceeding the scope of the claimed invention. In one series of modifications, clamps 10 and 14 are implemented in diverse ways other than in the mechanism of FIGS. 2 and 3. For example, clamps 10 and 14 may be devices, such as clamping forceps, which are separate from one another and control unit 26. Generally, the clamping action should pull blood vessel BV into a relatively thin tissue fold 18 to facilitate determination of differential waveform transmission over time.

In addition, the activation of source 22 and sensor 24 may be implemented manually, without switch 28. Even timer 30 might be omitted, with the timing being done by the user.

Accordingly, it is to be understood that the drawings and descriptions herein are proferred by way of example to facilitate comprehension of the invention and should not be construed to limit the scope thereof.

What is claimed is:

1. A method for measuring in vivo coagulation rate, comprising:

clamping a fold of organic tissues so that a target blood vessel contained in the organic tissues is closed at a downstream point and an upstream point spaced from one another;

after clamping the old of organic tissues, directing waveform energy through the fold of organic tissues; and analyzing waveform energy transmitted at least partially though the fold of organic tissues to determine a state of coagulation of blood trapped in the blood vessel between said downstream point and said upstream point.

2. The method defined in claim 1 wherein the clamping of the organic tissues comprises:

providing a first clamping element and a second clamping element; and disposing said first clamping element and said second clamping element on opposite sides of the fold of organic tissues.

3. The method defined in claim 2, further comprising the step of emitting the waveform energy from one of said first clamping element and said second clamping element.

4. The method defined in claim 3, also comprising the step of receiving the waveform energy transmitted through the fold of organic tissues by a sensor mounted to the other of said first clamping element and said second clamping element.

5. The method defined in claim 4 wherein the waveform energy is taken from the group consisting of electromagnetic radiation and mechanical vibrational energy.

6. The method defined in claim 5, further comprising the step of operating a source in said one of said first clamping element and said second clamping element to generate the waveform energy.

7. The method defined in claim 6 wherein the analyzing of the waveform energy includes the step of periodically comparing a current pattern of energy transmission with a reference pattern of energy transmission, thereby determining when blood trapped in said blood vessel between said downstream point and said upstream point begins to coagulate.

8. The method defined in claim 7 wherein the analyzing of the waveform energy further includes the step of measuring a time interval terminating with a detection of blood coagulation in the blood vessel between said downstream point and said upstream point.

9. The method defined in claim 1 wherein the analyzing of the waveform energy includes the step of periodically comparing a current pattern of energy transmission with a reference pattern of energy transmission, thereby determining when blood trapped in said blood vessel between said downstream point and said upstream point begins to coagulate.

10. The method defined in claim 9 wherein the analyzing of the waveform energy further includes the step of measuring a time interval terminating with a detection of blood coagulation in the blood vessel between said downstream point and said upstream point.

11. The method defined in claim 1 wherein the clamping of the fold of organic tissues includes the step of closing the blood vessel first at said downstream point and subsequently at said upstream point, thereby enabling a collection of an increased amount of blood in the blood vessel between said downstream and said upstream point.

12. The method defined in claim 11 wherein the clamping of the organic tissues comprises:

providing a first clamping element and a second clamping element; and disposing said first clamping element and said second clamping element on opposite sides of the fold of organic tissues;

said first clamping element and said second clamping element being parts of a single device, the clamping of the fold of organic tissues including the step of actuating said device to move said first clamping element and said second clamping element towards one another differentially at said downstream point and said upstream point.

13. The method defined in claim 1 wherein the waveform energy is taken from the group consisting of electromagnetic radiation and mechanical vibrational energy.

14. A device for measuring in vivo coagulation rate, comprising:

a first clamping element and a second clamping element;

an actuator mechanism operatively connected to said first clamping element and said second clamping element for shifting said first clamping element and said second clamping element towards one another, said first clamping element, said second clamping element, and said actuator mechanism being configured to clamp the blood vessel first at said downstream point and subsequently at said upstream point;

a source of waveform energy mounted to one of said first clamping element and said second clamping element;

a sensor of said waveform energy mounted to one of said first clamping element and said second clamping element; and an analyzer of said waveform energy operatively connected to said sensor for determining a time of onset of blood coagulation in a blood vessel clamped between a downstream point and an upstream point by said first clamping element and said second clamping element.

15. The device defined in claim 14 wherein said analyzer includes a patter comparator for periodically comparing a current pattern of energy transmission with a reference pattern of energy transmission, thereby determining when blood trapped in said blood vessel between said downstream point and said upstream point begins to coagulate.

16. The device defined in claim 15 wherein said analyzer further includes a timer for measuring a time interval terminating with a detection of blood coagulation in the blood vessel between said downstream point and said upstream point.

17. The device defined in claim 14 wherein said source and said sensor are disposed on different ones of said first clamping element and said second clamping element.

* * * * *